United States Patent [19]
Errico et al.

[11] Patent Number: 5,520,690
[45] Date of Patent: May 28, 1996

[54] ANTERIOR SPINAL POLYAXIAL LOCKING SCREW PLATE ASSEMBLY

[76] Inventors: Joseph P. Errico, P.O. Box 3070, Garden City, N.Y. 11531; Thomas J. Errico, 5 Crest Acre Ct., Summit, N.J. 07901; James Ralph, 71 Manito Ave., Oakland, N.J. 07436

[21] Appl. No.: 421,087

[22] Filed: Apr. 13, 1995

[51] Int. Cl.$^6$ ........................................ A61B 17/70
[52] U.S. Cl. ........................ 606/61; 606/69; 606/70; 606/73
[58] Field of Search ........................ 606/61, 69, 70, 606/71, 72, 73, 75, 76, 104; 623/17, 16

[56] References Cited

U.S. PATENT DOCUMENTS

| | | | |
|---|---|---|---|
| 5,053,036 | 10/1991 | Perren et al. | 606/69 |
| 5,057,111 | 10/1991 | Park | 606/69 |
| 5,147,361 | 9/1992 | Ojima et al. | 606/61 |
| 5,180,381 | 1/1993 | Aust et al. | 606/61 |
| 5,269,784 | 12/1993 | Mast | 606/69 |
| 5,324,290 | 6/1994 | Zdeblick et al. | 606/61 |
| 5,429,639 | 7/1995 | Judet | 606/61 |

FOREIGN PATENT DOCUMENTS

| | | | |
|---|---|---|---|
| 9416634 | 8/1994 | WIPO | 606/69 |

OTHER PUBLICATIONS

"Cervi–Lok Cervical Fixation System", Spinetech, Inc., 980 East Hennepin Ave., Minneapolis, Minn 55414, 1994., 2 pages.

"System Overview—Axis Fixation System", Sofamor Danek, 1800 Pyramid Place, Memphis Tenn 38132, 1994, 6 pages.

"Surgical Technique—Orion Anterior Cervical Plate System", Sofamor Danek, 1800 Pyramid Place, Memphis Tenn 38132, 1994, 25 pages.

"Surgical Technique—ZPlate-ATL Anterior Fixation System", Sofamor Danek, 1800 Pyramid Place, Memphis Tenn 38132, 1994, 27 pages.

*Primary Examiner*—Guy Tucker
*Attorney, Agent, or Firm*—J. P. Errico

[57] ABSTRACT

The present invention is a polyaxial locking screw plate assembly for immobilization of vertebral bones, via fixation to surfaces thereof. In one embodiment the invention includes a plate, having an upper portion and a lower portion, each of which has a pair of threaded holes, into which holes coupling elements may be screwed. The coupling elements each have a threaded cylindrical exterior, and have an interior semi-spherical concave surface in which the semi-spherical head of a bone screw may be polyaxially mounted. In a second embodiment, the present invention includes a similar plate, having holes which are, however, threaded part of the way through the plate. In this embodiment, the bottom portion of the holes of the plate, additionally, have a curved interior surface which forms an annular lip for supporting a semi-spherical head portion of a bone screw. The coupling element of this embodiment is a short threaded cylindrical piece, having a concave bottom which locks the screw into the hole. Variations of each embodiment have means associated with the holes and/or the coupling element for locking the angle of the screw to the plate. A further variation of the plate of this invention includes a pair of spikes which may be used to temporarily lock the plate to the exposed bone.

17 Claims, 9 Drawing Sheets

ANTERIOR SPINAL POLYAXIAL LOCKING SCREW PLATE ASSEMBLY

BACKGROUND OF THE INVENTION

1. Field of the Invention

This invention relates generally to a spinal implant assembly for holding adjacent vertebral bones fixed. More particularly, this invention relates to a novel assembly of bone screws and plates for use in surgical procedures for stabilizing the relative motion of, or permanently immobilizing, vertebral bodies, wherein the screws form a polyaxial coupling of the plate to the bone, and which maintains a flush exterior plate surface through a wide range of entrance angulation.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Referring now to FIGS. 1 and 2, a typical vertebral body is shown in a top view and a side view. The spinal cord is housed in the central canal 10, protected from the posterior side by a shell of bone called the lamina 12. The lamina 12 has three large protrusions, two of these extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. The use of screw plate assemblies for stabilization and immobilization via lateral or anterior entrance is, however, common.

Because the spine is routinely subject to high loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied. It has, therefore, been an object of those in the art to provide a screw plate assembly which permits the screws to be entered into the vertebral body at angles other than 90 degrees.

A great concern, however, with screws being implanted in the anterior portion spine, most particularly in the cervical spine, is that their are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate. Breaches of the esophageal wall permit bacterial contamination of the surrounding tissues, including the critical nerves in and around the spinal cord. Such contamination can be fatal. Because screw pull-out represents one of the largest risks of esophageal perforation, it has been an object of those in the art to produce a cervical screw plate design having a locking means which couples, not only the plate to the bone, but locks the screw to the plate. In such a design, it is intended that, even if the bone holding the screw fails, the screw will not separate from the plate.

In addition to pull-out, however, it has been observed that if the screw plate design includes screw heads which protrude beyond the exterior surface of the plate, long term wearing of surrounding tissues may occur, leading to the development of abscesses and holes, which, once again, can have grave consequences. With respect to cervical plates, which are necessarily thin, on the order of a few millimeters, unless the system is designed to specifically accommodate non-perpendicular screw-in directions, the heads of the screws which are desirably toe-nailed in are a considerable risk.

Similar concerns exist in the thoracic and lumbar regions with respect to anterior and lateral fixation implants as their are proximally located organs as well as a plurality of major blood vessels which may be compromised by either catastrophic screw pull-out and/or long term wearing of non-flush surface protrusions.

One screw plate design which has been offered to provide physicians and patients with a reduced risk of pull-out or damage to proximal tissues is the Orion (Reg. Trademark) Anterior Cervical Plate System of Sofamor Danek USA, 1800 Pyramid Place, Memphis, Tenn. 38132. The Orion™ system teaches a plate having two pair of guide holes through which the screws are inserted to fix the plate to the vertebral body. The plate further includes external annular recessions about each of the guide holes which are radially non-symmetric in depth. More particularly, the annular recessions serve as specific angle guides for the screws so that they may be inserted non-perpendicularly with respect to the overall curvature of the plate. In addition, the Orion™ plate includes an additional threaded hole disposed between each of the pairs of guide holes so that a corresponding set screw may be inserted to lock the bone screws to the plate.

Although the Orion™ system achieved certain advantages over prior cervical screw plate assemblies, it is not without failures. Specifically, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

It is further a failure of the Orion™ system that an extra set screw is required to lock the screw to the plate. Plates for use in the cervical spine are very thin, and if the screw head already rests in an annular recess, and there is to be enough room for the head of the set screw to rest on top of the head of the bone screw, the thickness of the remaining plate must be reduced even further. The thinner the plate is at the load bearing points—the guide holes—the weaker the plate is overall.

While the preceding discussion has focused on a specific cervical screw plate system and its failures, the same failures apply to the art of vertebral immobilizing screw plate systems which are presently available as well. There are no presently available screw plate assemblies which present a flush surface and provide for means of preventing both screw pull-out from the bone and screw backout from the plate, while simultaneously providing for a wide range of angulation for the bone screws.

An additional concern for physicians who implant screw plate assemblies for spinal fixation is proper alignment for pre-drilling of the holes into which the bone screws are driven to hold the plate. As suggested above with respect to the angulation of the annular recesses of the Orion™ system, the process of forming the holes generally involves placing the plate against the appropriate vertebral bodies and using a guide to hold the proper angle with respect to the plate and bone as a drill is used. The difficulty in this process involves slippage at the interface between the unsecured plate and the bone. To avoid slippage, the surgeon is generally required to use, simultaneously, a plate holding mechanism, which may be removable affixed to the plate, to maintain the plate in its proper position, a drill guide to set the desired angulation (which is set by the thread angle of the plate), and the drill itself. It is understood that simultaneous manipulation of these three tools by the surgeon is tedious and difficult.

It is therefore, an object of the present invention to provide a new and novel cervical, thoracic, and/or lumbar screw plate design having a polyaxial coupling of the screw to the plate, whereby a single plate is compatible with a wide range of screw-in angles.

It is also an object of the present invention to provide a screw plate design having a flush exterior while being fixed to the vertebral bodies which it immobilizes; having no screw head protrusion despite non-perpendicular angulation.

It is also an object of the present invention to provide a spinal insert assembly which is more sturdy and more versatile than previous designs.

Further, it is an object of the present invention to provide a screw plate design which provides the surgeon with the greatest freedom to choose the most desirable angle to direct the bone screw.

It is also an object of the present invention to provide an orthopedic screw plate assembly which has a simple and effective locking mechanism for locking the bone screw to the plate.

It is also an object of the present invention to provide a screw plate assembly which has a simple and effective means of holding the plate in position for the pre-drilling of screw holes.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flush locking polyaxial screw plate assembly for use in stabilizing and immobilizing vertebral bodies. The assembly comprises a plate having a set of threaded holes, bone screws having a semi-spherical top portion, and a coupling element. The coupling element has an external threading for insertion and locking into the holes of the plate and also has a bottom surface for compressing and holding the semi-spherical top portion of the bone screw. In preferred variations, the plate further includes a set of spikes on the surface which interfaces with the bones, for holding the plate in position during the pre-drilling step.

The present invention has a variety of embodiments, the first of which is summarized hereinbelow. The plate is a flat metal element, having a rectangular shape with rounded corners, contoured to the curved cylindrical surface of the vertebral bodies to which it is secured. There are four threaded holes disposed at the four corners of the plate which extend through the plane of the plate, positioned so that they are aligned in pairs with the vertebral bodies to which the plate is to be attached. The threading and shaft portion of the bone screws may be of a variety of standard designs, or a particular design which may be found more secure than the standard ones. The head, however, is not standard in that it comprises a semi-spherical section.

For the purposes of inserting the screw into the bone, the head comprises a recessed region such as a slot, phillips, star, or hexagonal recesses which are ideally suited for mating to an appropriate screwdriving tool. The recess, however, shall not alter the exterior radially semi-spherical shape of the head.

The coupling element comprises a socket for holding the ball head of the screw, and an exterior threading which mates with the threaded holes of the plate. The first step in the process of implanting this embodiment of the invention is to position the plate against the vertebral bodies and to align the entry points for the screws. The next step is to pre-drill the holes into the bones at the desired angle, into which the screws will be inserted. With the plate in place, the screws may now be inserted through the holes in the vertebral bodies.

The coupling element must either provide a recess which may be positioned co-linearly with the recess in the screw head for screwing in the screw, or it must be partially open so that the screw and coupling may be manipulated easily so that the recess in the head of the screw is accessible. In either variation, once the screw has been fully inserted into the bone, at the desired angle, the coupling element, via its rotationally free mating of the socket to the inserted screw, is realigned so that it may be locked down into the plate. Screwing down the coupling provides the locking coupling of the screw to the plate, whereby the screw may be angled non-perpendicularly with respect to the plate, while the coupling element is flush with the external surface of the plate, and without the need for a set screw.

In a preferred variation of this embodiment, the socket of the coupling element includes vertically oriented slots so it may be crush-locked to the ball head of the screw by the application of a radial force. In addition, the threaded holes of the plate element are tapered so that by screwing the coupling into the plate, the tapering has the effect of applying a radial force to the slotted socket portion of the coupling. This circumferential reduction has the desirable effect of locking the screw at the insertion angle. In this way, the coupling element serves as an additional support for keeping the screw in the bone at the proper angle.

In this embodiment the coupling device permits the ball head of the screws to be locked to the plate independent of the insertion angle of the screw. The first embodiment locks the screw head to the plate, but still permits rotational motion of the screw; the second locks the screw to the plate and locks the screw to its appropriate angle. The additional ability to lock the ball head of the screw to the coupling element and plate may be desirable for some patients, such as adult patients for whom the natural settling of the screw in the vertebral bone is not a concern. For those patients for whom screw settling is anticipated, the first embodiment may be more appropriate.

It is understood that the variations in the coupling element (with respect to its recessed or open top) have been provided so that the polyaxial screw may be used with cervical, thoracic, and lumbar plates, despite the considerable variation in plate thicknesses.

Another embodiment of the present invention comprises a plate, similar to the one described above, wherein the holes are threaded only partially through the plate. The unthreaded portion of the hole forms an annular curved lip at the bottom of the hole which forms a cup shaped support which is ideally suited for supporting the semi-spherical ball top of the screw while simultaneously permitting rotational motion whereby the entrance angle of the screw may be varied through a wide range. In this embodiment the coupling element comprises a concave bottom portion, a threaded exterior cylindrical sidewall, and a flat top. This coupling element is locked into the hole by being screwed into position, forming a flush external surface of the plate and holding the screw in the plate. The coupling element may also have a downward directed spike, or similar means, for locking the screw both into the plate and into its preferred angulation.

All embodiments and variations of the present invention may include a spike, or set of spikes, which extend outward from the bottom surface of the plate (the surface which interfaces with the bone surface of the vertebral bodies). During implantation, and more particularly during the step of pre-drilling the holes into the bones, the plate may be held firmly in place by simply positioning the plate and applying enough pressure to drive the spikes into the bone. The spikes will hold the plate in position, thereby freeing the hands of the surgeon to easily and accurately pre-drill the ideally angled holes. The spikes also provide supplementary gripping and holding strength for the plate, in addition to the screws once the plate assembly has been implanted securely.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 2:
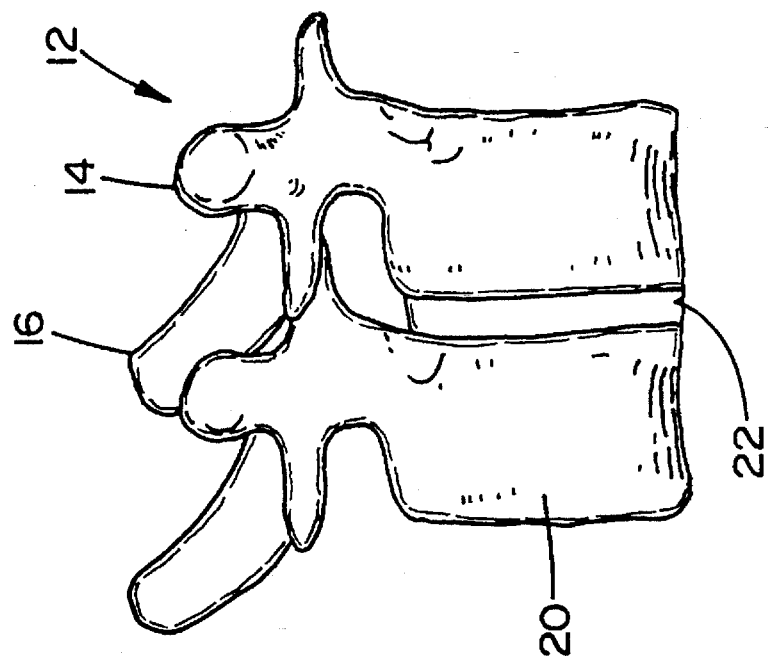
FIG. 2 is a side view of sequentially aligned vertebral bones.
Figure 1:
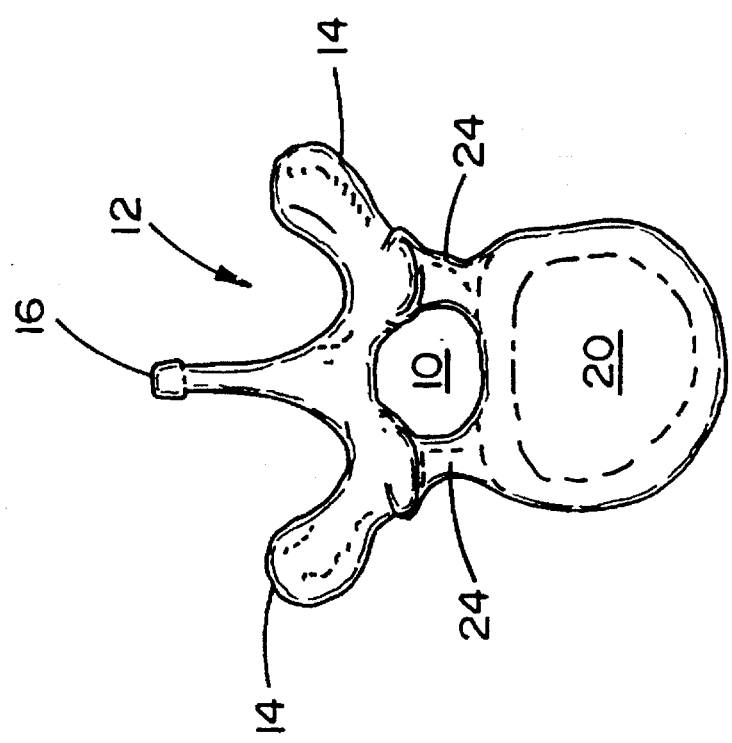
FIG. 1 is a top view of a vertebral bone, the stabilization of which the present invention is directed.
Figure 3:
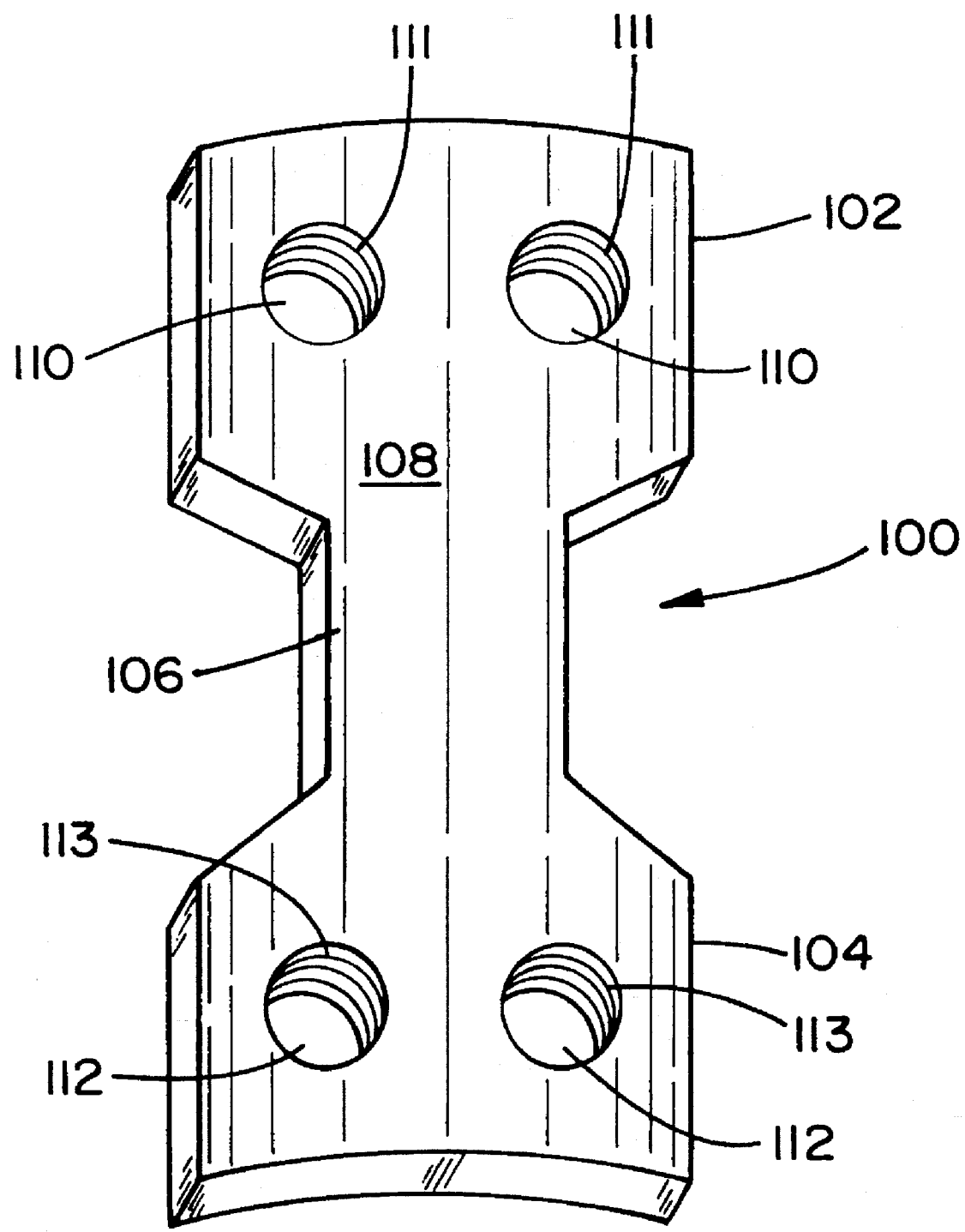
FIG. 3 is a perspective view of a locking plate which is an element of one aspect of the present invention.

Referring now to FIG. 3 a plate which is an element of the present invention is shown in a perspective view. The plate 100 may be constructed of any suitably biocompatible material which has the structural strength and durability to withstand the cyclical loading associated with long term fixation to the spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

The plate 100 comprises upper and lower portions 102, 104 respectively, which are connected by a narrow region 106, therein being generally I-shaped. The plate 100 also has a top surface 108 and a bottom surface (not shown). A slight curvature is imparted to the plate 100 so that it may grossly conform to the cylindrical morphology of the vertebral bodies which it couples. As shown in FIG. 3, the external surface 108 is the convex surface, the internal surface is concave.

A pair of holes 110, having internal threading 111, which extend fully through the plate, from the upper surface 108 through the lower surface, are disposed in the upper portion 102. A second pair of holes 112, having internal threading 113, having internal threading 111 as well, are disposed in the lower portion 104 of the plate 100. Each of the holes 110,112 is ideally suited for receiving therethrough a bone screw for affixing the plate to the vertebral bodies.

Figure 4:
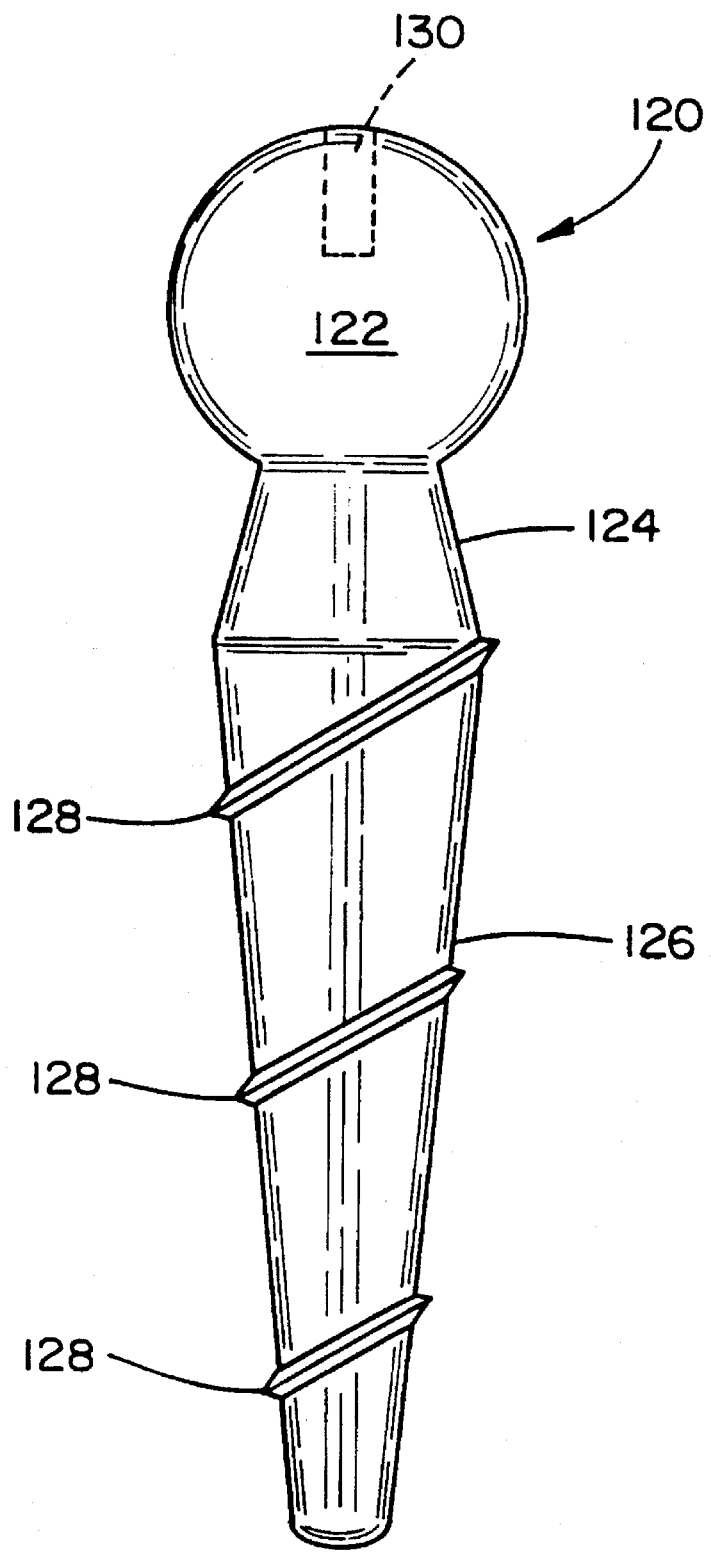
FIG. 4 is a perspective view of a bone screw which is an element of one aspect of the present invention.

Referring now also to FIG. 4, a screw of a type which is ideally suited for coupling the plate 100 to vertebral bones is shown in a side view. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the coupling element (as described with respect to FIGS. 5a and 5b) to be screwed into the appropriate hole 110 or 112 of the plate 100 and remain coupled to the head 122.

Figure 5B:
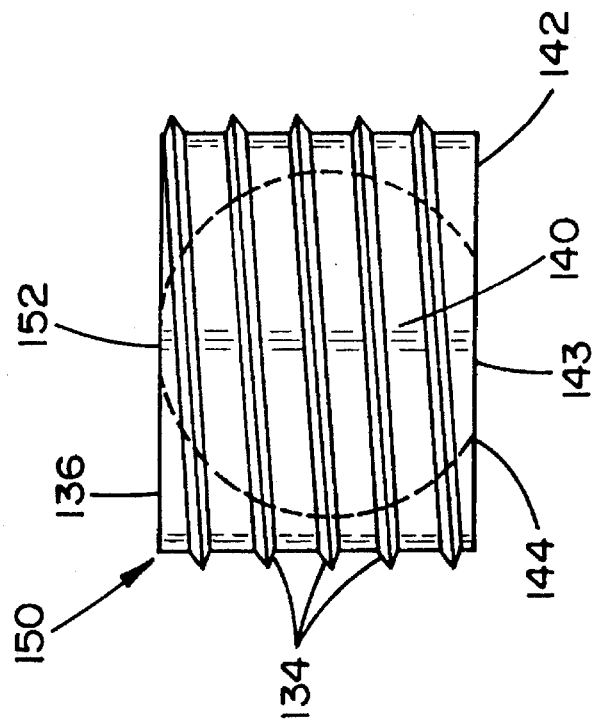
FIGS. 5a and 5b are perspective views of coupling elements which are aspects of embodiments of the present invention.
Figure 5A:
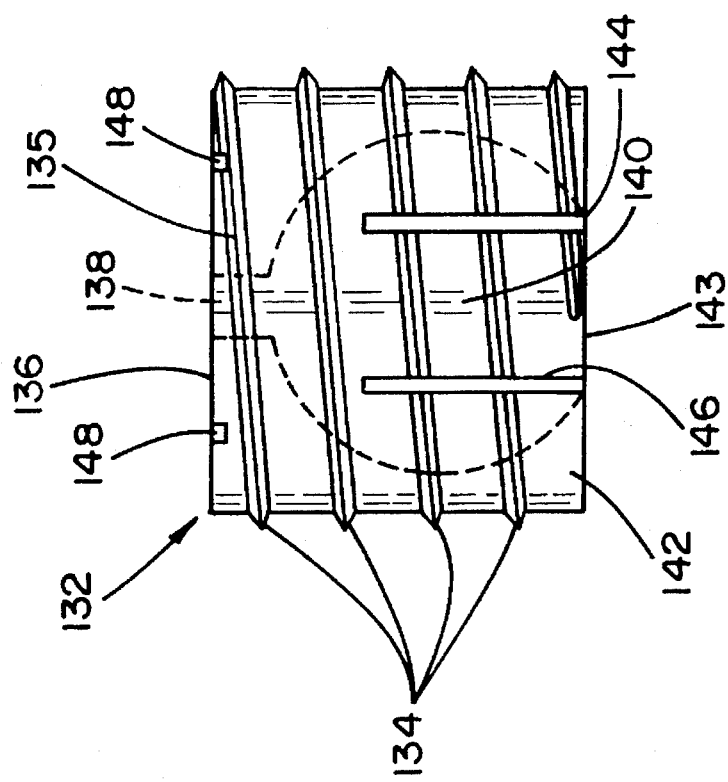

Referring now also to FIGS. 5a and 5b, two variations in the coupling element of the present invention are shown in side views, wherein phantom lines show the interior structure of the elements along a diametrical cross section. With specific reference to FIG. 5a, coupling element 132 comprises a cylindrical socket having an external threading 134. The threading 134 and the diameter of the exterior of the cylinder is designed to mate with threading 111 or 113 of the holes 110 or 112 of the plate 100, so that the coupling element 132 may be screwed into the plate 100. It is preferable that the uppermost thread 135 be designed to crush-lock the coupling element 132 into the hole 110 or 112. Once screwed into the plate 100, and locked down, the top surface 136 of the coupling element 132 and the top surface of the plate 108 present a flush external surface.

The top surface 136 of the variation of the coupling element 132, which is shown in FIG. 5a, further comprises a through hole 138, which extends from the top surface 126 to an interior semi-spherical volume 140. This through hole 138 is designed such that the screwdriving tool which is used to insert the screw 120 into the bone may access and rotate the screw 120 through the coupling element.

The interior semi-spherical volume 140 is ideally suited for holding the head portion 122 of the screw 120, and permitting the screw to rotate through a range of angles. The coupling element 132 has a bottom 142 which has a circular hole (enumerated as 143 on the bottom surface of the side view of the coupling element in FIG. 5a) which forms the bottom entrance into the interior semi-spherical volume 140. It is understood that the head 122 of the screw 120 is held within the interior semi-spherical volume 140 by the annular rim, or support lip, 144 of the bottom 142 of the coupling element 132. This annular support lip 144 defines the circular opening 143 which has a diameter less than the diameter of the semi-spherical head 122 of the screw 120.

It is, therefore, preferred that the lower portion of the coupling element 132 comprise slots 146 so that the physician may insert the head portion 122 into the interior volume 140. These slots 146 permit the lower portion of the coupling element 132 expands to accept the inserted head portion 122, but is secured from releasing the head 122 once the coupling element 132 is screwed into the plate 110a. In an alternative variation, the holes 110 or 112a (as shown in phantom in FIG. 6) of the plate 100 are tapered inward with respect to insertion direction. In such a variation, the step of screwing the coupling element 132 into the hole 110a or 112a causes the slots 146 to be compressed and, correspondingly, for the bottom entrance 143 and the annular lip 144 to lock the screw head into position.

In the alternative, it is also possible for the coupling element to be formed in a manner whereby the lower portion does not have to include an expanding entrance 143. In such a variation, the coupling element would necessarily be formed of two separate pieces which would be joined together about the head 122 of the screw. In either design, however, it is preferred than the top surface 136 of the coupling element 132 have means, such as holes 148, for a second screwdriving tool to easily insert the element 132 into the threaded holes 111 or 113 of the plate 100.

Referring now to FIG. 5b, an alternative coupling element 150 is shown in a side view, wherein phantom lines correspond to internal features of the coupling element taken along the diametric cross section. This coupling element 150 is similar in most respects to the coupling element 132 of FIG. 5a, in that it is a threaded cylindrical body, having a top surface 136 and a bottom surface 142, the bottom surface 142 having an entrance hole 143, defined by an annular lip 144, which opens into an interior semi-spherical volume 140. The significant difference between this variation 150 and the coupling element 132 of FIG. 5a is that the top surface 136 of this variation 150 does not include an extending through hole 138 for receiving therethrough a screwdriving tool, but rather has a circular opening 152 through which the top of the head 122 of the screw 120 may protrude slightly.

The variation of the coupling element 150 is a cylindrical body which may be shorter from top surface 136 to bottom surface 142 than the coupling element 132 of FIG. 5a. This shorter coupling element 150 is preferably utilized in the cervical spine as it is more compatible with a lower profile cervical plate. Thicker coupling elements are more compatible with thicker plates of the thoracic and lumbar spine.

Figure 6:
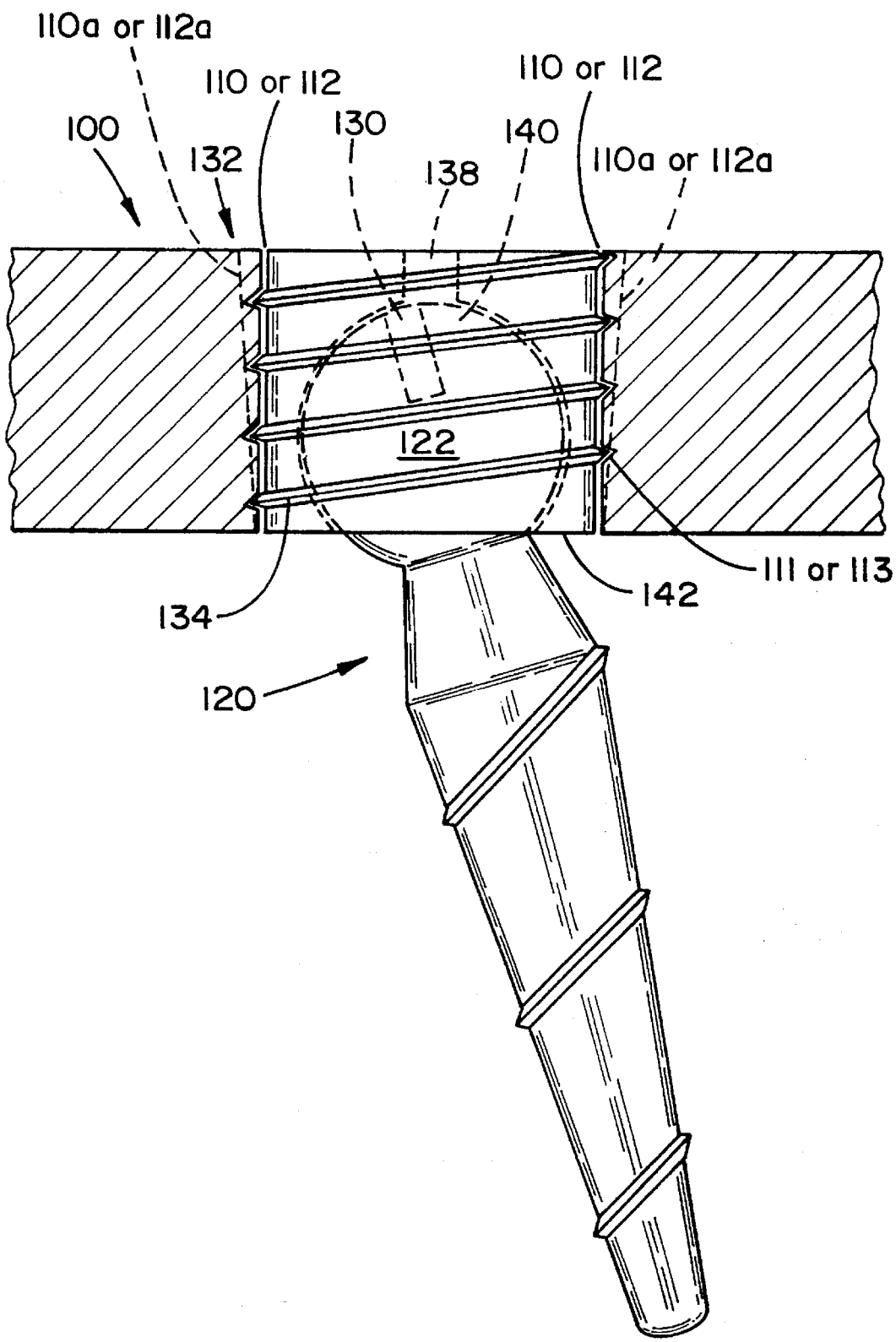
FIG. 6 is a side cross sectional view of one embodiment of the present invention in a fully assembled form.

Referring now to FIG. 6, a cross sectional view of a fully assembled screw plate assembly of the present invention is shown. With reference to the relative positions of the screw 120, plate 100, and coupling element 132, the operative steps of implanting this screw plate assembly and affixing it to a pair of vertebral bones begins with preparing the bones through surgical tissue resection and exposure. Next the plate 100 is positioned against the bones and pre-drill holes are made at the desired insertion angle for the screw 120. Screw 120 and coupling element 132 are then placed together so that the head 122 is within the interior volume 140, whereby the two elements are able to rotate freely with respect to one another, but are nonetheless coupled.

The recess 130 in the screw 120 and the through hole 138 of the coupling element 132 are aligned at first, and an appropriate screwdriving tool is used to insert the screw 120 through the proper hole 110 or 112 (110a or 112a) and into the pre-drilled hole in the bone. Once the screw 120 has been screwed down to the point that the bottom surface of the coupling element 142 contacts the plate 100, the first threads 134 of the coupling element are mated to the threading 111 or 113 of the hole 110 or 112 (110a or 112a), respectively.

Complete insertion of the coupling element 132 to the plate 100, preferably locks the element to the plate, in addition to locking the screw 120 and plate 100 to the bone. In the variation of the embodiment in which the coupling 132 has slots (elements 146 of FIG. 5a) and an expanding bottom entrance 143, corresponding holes 110 or 112 (110a or 112a) may be tapered; the complete insertion of the coupling element 132 into the hole 110 or 112 therein having the additional benefit of locking the angle of the screw 120.

Figure 7:
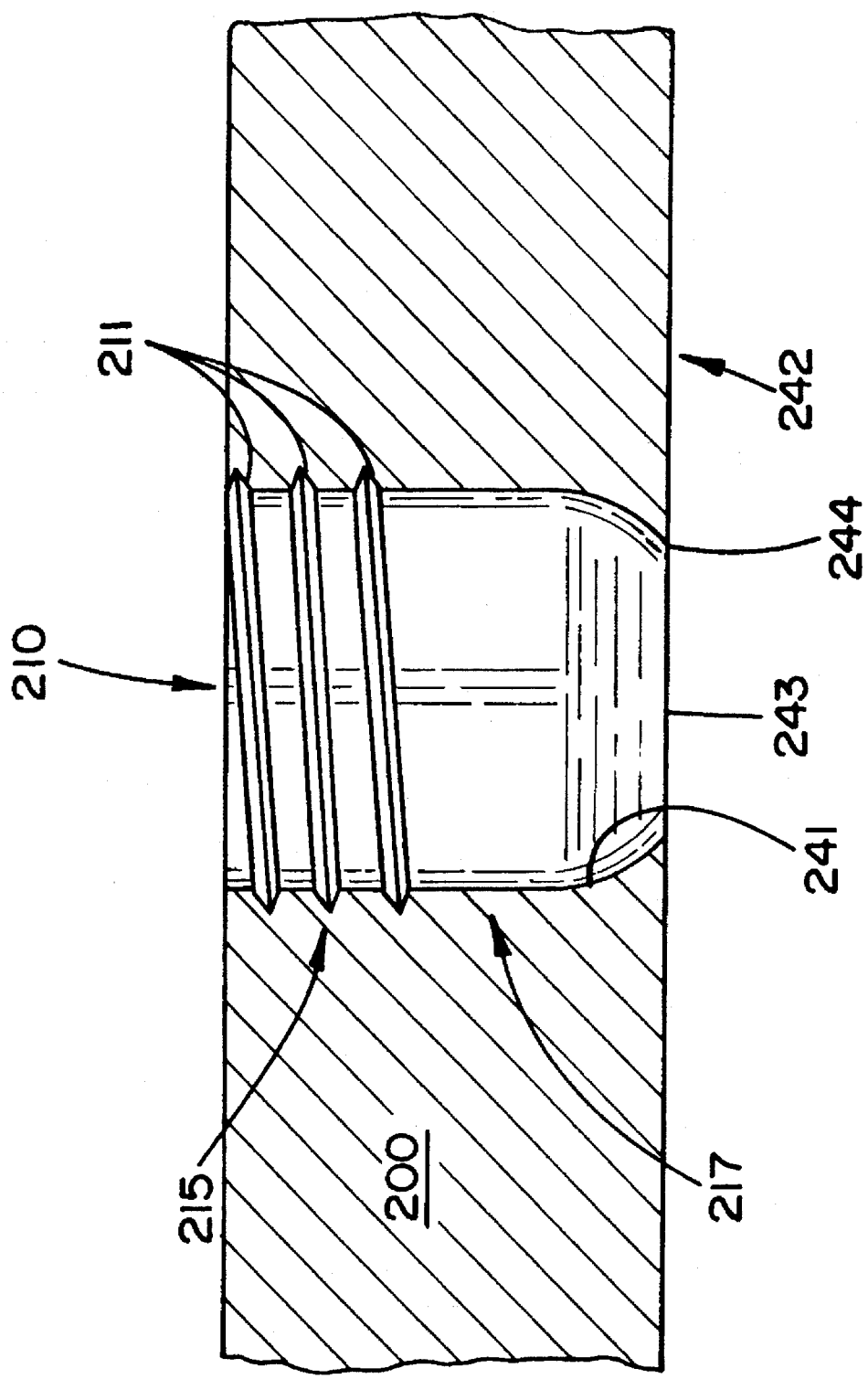
FIG. 7 is a side cross sectional view of the plate of another embodiment of the present invention.

Referring now to FIGS. 4, 7, 8a, 8b, and 9, an alternative embodiment of the present invention is now described. Referring specifically to FIG. 7, a cross sectional view of a hole 210 in a plate 200, which is similar to the plate 100 of the first embodiment (shown in FIG. 3), is shown. The hole 210 is generally cylindrical and comprises an upper portion 215 and a lower portion 217. A threading 211 is provided in the upper portion 215. The lower portion 217 of the hole 210 is curved inward, the diameter of the hole decreasing from the interface of the upper and lower portions of the plate 200 to the bottom 242.

Referring now also to FIG. 4, the curvature of the inner surface 241 of the lower portion of the hole 210 is set to match the semi-spherical head 122 of the screw 120. The bottom of the hole 243 is defined by an annular lip 244 which supports the screw 120 once it is inserted through the hole 210. The diameter of the bottom of the hole 243 is larger than the diameter of the neck 124 of the screw 120, but is less than the diameter of the head 122. This permits the screw 120 to be inserted at an angle through the plate, and into the bone. The maximum angle permitted is understood to be the angle at which the neck 124 of the screw 120 contacts the annular lip 244 of the plate 200.

Figure 8A:
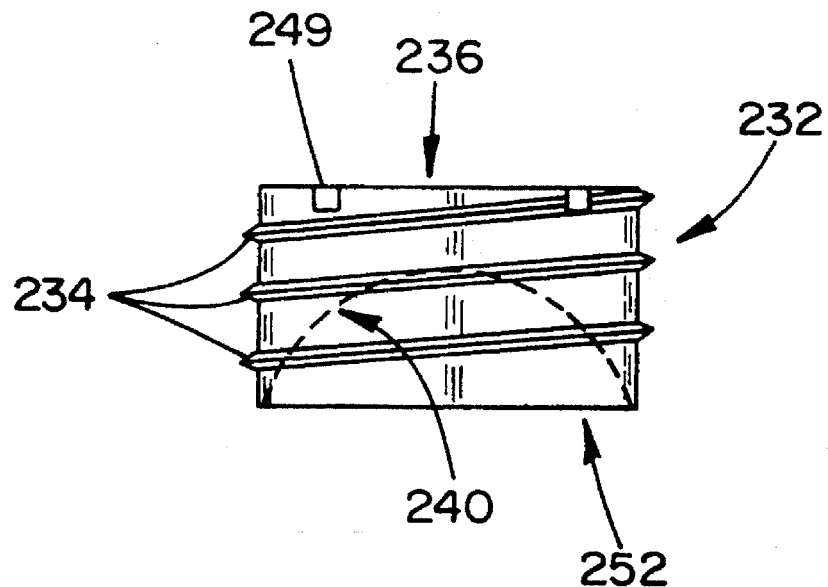
FIGS. 8a and 8b are side cross sectional views of coupling elements of another embodiment of the present invention.
Figure 8B:
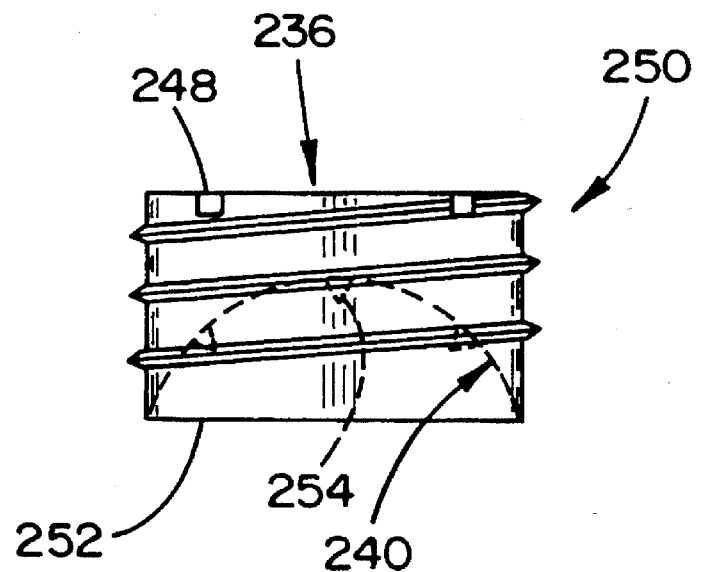

Referring now also to FIGS. 8a and 8b, alternative coupling elements 232 and 250, respectively, which are for locking the screw 120 to the plate 200, are provided in side views having phantom lines showing the diametric cross sectional features of each element. Specifically with respect to FIG. 8a, the coupling element 232 comprises a cylinder having threads 234 on its outside surface. The diameter and threads 234 of the element are chosen so that the element may be inserted into the appropriate hole 210 of the plate 200, and therewith form a flush external surface of the plate. The top surface 236 of the element includes suitable recesses 248 which mated with a screwdriving tool for insertion of the element 232 into the plate 200.

The bottom 252 of the coupling element comprises a concave semi-spherical surface 240. The radius of curvature of the concave surface 240 is preferably equivalent to the surface of the head portion 122 of the screw 120. This contour permits the flush insertion of the coupling element 232 into the hole 210, for the purposes of locking the screw to the plate, without forcing the screw into any specific angulation. In this specific variation of this embodiment, the screw 120 is locked to the plate 200 with respect to its depth, but still remains rotationally free. This may be desirable for patients in which considerable settling is expected as the bone tissue conforms to the inserted screw.

For patients in whom less settling of the screw within the bone is anticipated, a different variation of the coupling element is provided. Specifically referring to FIG. 8b, a coupling element 250 is shown in a side view having phantom lines corresponding to features of the element 250 along the diametric cross section. The concave semi-spherical surface 240 of this variation is provided with protuberances 254, for example small spikes or other grasping and locking means, which are capable of holding the head 122 of the screw 120 in a fixed angulation as well as locking the screw to the appropriate depth.

Figure 9:
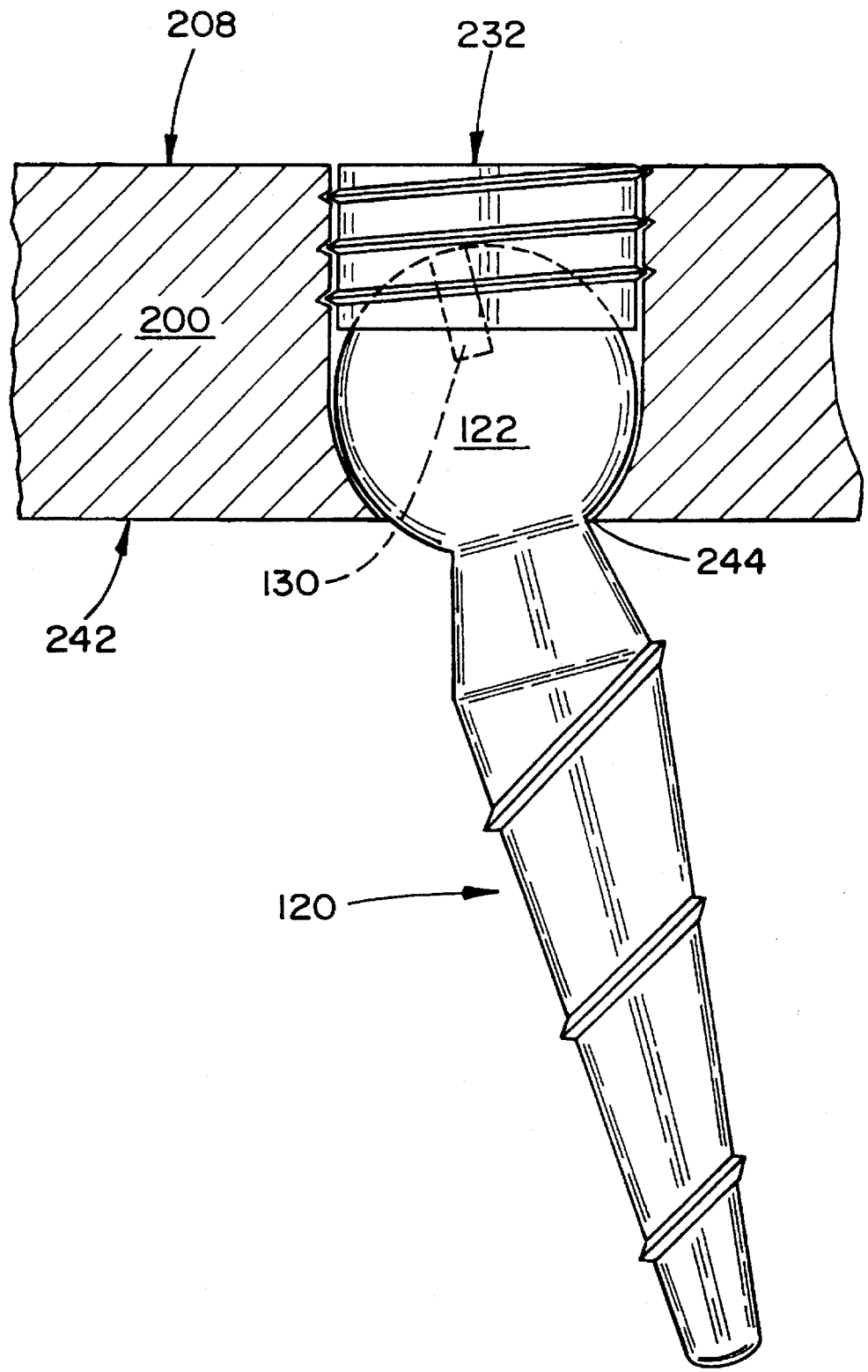
FIG. 9 is a side cross sectional view of another embodiment of the present invention in a fully assembled form.

Referring now to FIG. 9, a side cross sectional view of a portion of the fully assembled embodiment of the present invention is shown. The operative sequence of steps for implantation of this device begins with the surgical exposition, final analysis, and preparation of the vertebral bodies. Once the appropriate decisions with respect to screw angulation and coupling variant have been made, the plate 200 is positioned across the exposed surfaces of the bones. Pre-drill holes are made into the bones at the desired angle, and the screws 120 are inserted with the use of a screwdriving tool mated to the recess 130 in the head 122. Once the screw 120 has been inserted, and the head 122 is properly supported by the annular lip 244 of the plate bottom 242, the coupling element 232 is screwed into the plate until the top portion of the coupling element is flush with the external surface 208 of the plate 200. In this position, the concave semi-spherical surface 240 of the bottom of the coupling element and the curved lower portion 241 of the hole 210 in the plate 200 define therebetween the volume in which the head 122 of the screw 120 is locked. As described above, it may be preferred that the surface of the head 122 of the screw 120 and the concave semi-spherical surface 240 of the coupling element 232 may lock together to fix the angle of the screw 120 with respect to the plate 200 once the coupling element 232 has been locked down.

Figure 10:
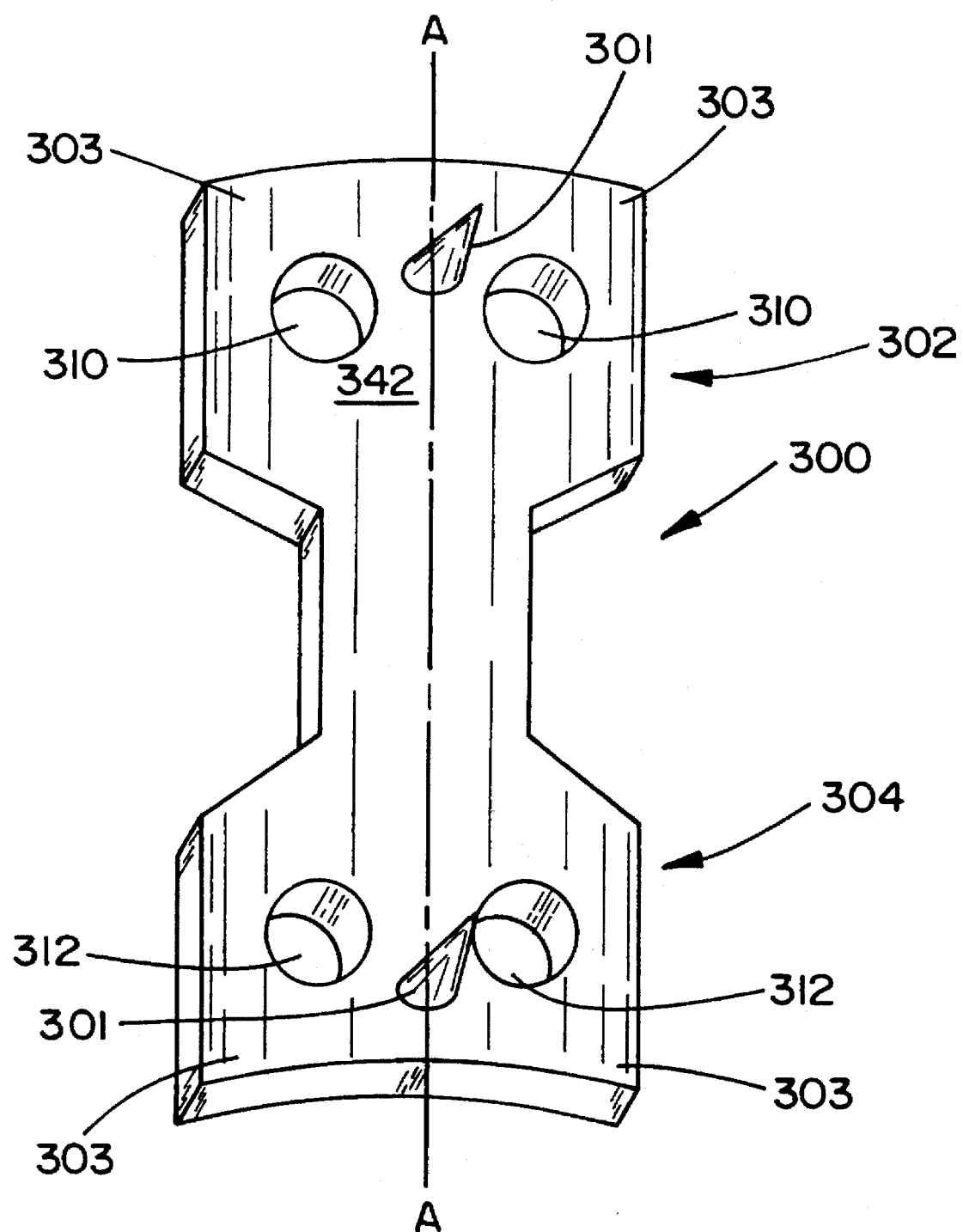
FIG. 10 is a side view of a plate which includes a variation of the present invention.

Referring now to FIG. 10, a variation of the plate of the present invention is shown a in perspective view. The plate 300, which comprises the same pairs of holes 310 or 312 in the upper and lower portions 302 and 304, respectively, further includes at least one spike element 301 which protrudes from the bottom surface 342 of the plate 300. In a preferred aspect, the plate 300 has two spikes 301, each positioned between the pair of holes 310 or 312, on center line A—A. These spikes provide means for temporarily, and easily removably, fixing the plate 300 to the bone during the steps of pre-drilling and insertion of the screws through the plate and into the bone. This is a desirable operational advantage, as it frees one hand of the surgeon and/or removes extra tools from the surgical site.

It is preferred to have the spikes positioned along the center line A—A for plates 300 which have a radius of curvature which is equal to or greater than that of the vertebral bodies (not as curved as the bone). Having the spikes along the center line ensures that the plate can be removably fixed to the bone by simply applying an insertion force against the plate, driving the spikes into the bone. It is understood that for implants wherein the plate 300 has a smaller radius of curvature than the bone, it would be desirable to position the spikes at the corners 303 of the plate 300.

While there has been described and illustrated implantation devices for stabilizing and immobilizing regions of the spine by affixing a polyaxial locking screw plate to the anterior portion of the vertebral bones, it will be apparent to those skilled in the art that variations and modifications are possible without deviating from the broad spirit and principle of the present invention which shall be limited solely by the scope of the claims appended hereto.

We claim:

1. A polyaxial locking screw plate assembly for the immobilization of vertebral bones, via fixation to surfaces thereof, comprising:

a plate having an upper portion and a lower portion, said upper and lower portions each having at least one through hole;

a plurality of coupling elements, having a semi-spherical interior volume, each of said coupling elements being insertable into a corresponding through hole; and a plurality of bone screws, each of said bone screws having a semi-spherical head portion and a shaft, said shaft portion being insertable through the corresponding through hole and into the vertebral bone, and said semi-spherical head portion being rotationally freely mounted within the semi-spherical interior volume of the coupling element prior to insertion and such that the shaft of the bone screw and the coupling element may be inserted into a corresponding through hole and said shaft of the bone screw may be inserted into the vertebral bone at a selected angle within a predetermined range of angles including non-perpendicular angles relative to the plate and thereby locking said coupling element and said semi-spherical head to said plate at said selected angle as said semi-spherical head and said coupling element are advanced into said corresponding through hole.

2. The polyaxial locking screw plate assembly as set forth in claim 1, wherein said at least one through hole of each of said upper and lower portions of said plate comprises a pair of through holes.

3. The polyaxial locking screw plate assembly as set forth in claim 2, wherein each of said pair of through holes of each of said upper and lower portions of said plate includes an interior surface threading, and wherein each of said coupling elements includes an exterior surface threading which is matable to said interior surface threading, whereby each of said coupling elements is insertable into said corresponding through hole via engagement of said interior and exterior surface threadings.

4. The polyaxial locking screw plate assembly as set forth in claim 1, wherein said interior semi-spherical volume is defined by a curved interior surface, which forms a receiving socket into which the semi-spherical head portion is inserted whereby the head portion of said screw is rotationally freely mounted in said coupling element.

5. The polyaxial locking screw plate assembly as set forth in claim 4, wherein the curved interior surface of said coupling element further comprises slots which permit the interior semi-spherical volume to expand thereby facilitating the insertion of said semi-spherical head portion of said screw therein.

6. The polyaxial locking screw plate assembly as set forth in claim 5, wherein the corresponding through hole into which the coupling element is inserted is tapered inwardly, thereby causing, upon insertion of said coupling element into said corresponding through hole, the slots to be compressed, which causes the curved interior surface of the coupling element to lock the semi-spherical head portion of the screw at a definite insertion angle.

7. The polyaxial locking screw plate assembly as set forth in claim 1, wherein the head portion of each of said screws comprises a recess to which a screwdriving tool is matable for inserting said screw through the corresponding hole and into the vertebral bone.

8. The polyaxial locking screw plate assembly as set forth in claim 7, wherein each of said coupling elements comprises a top surface recess, through which said screwdriving tool may be inserted, and which top surface recess may be aligned with the recess in the head of the screw, by which screwdriver the screw may be inserted into the vertebral bone.

9. A polyaxial locking screw plate assembly for the immobilization of vertebral bones, via fixation to surfaces thereof, comprising:

a plate having an upper portion, a lower portion, a top surface and a bottom surface, said upper and lower portions each having at least one through hole;

a plurality of coupling elements, having a semi-spherical interior volume, each of said coupling elements being insertable into a corresponding through hole; and a plurality of bone screws, each of said bone screws having a semi-spherical head portion and a shaft, said shaft portion being insertable through the corresponding through hole and into a vertebral bone, and said semi-spherical head portion being polyaxially supported within the semi-spherical interior volume of said coupling element prior to insertion, such that the shaft of the bone screw and the coupling element may be inserted into a corresponding through hole and said shaft of the bone screw may be selectively angulated within a predetermined range of angles including non-perpendicular angles relative to the plate and thereby locking said coupling element and said semi-spherical head to said plate at said selected angle as said semi-spherical head and said coupling element are advanced into said corresponding through hole.

10. The polyaxial locking screw plate assembly as set forth in claim 9, wherein said at least one through hole of each of said upper and lower portions of said plate comprises a pair of through holes.

11. The polyaxial locking screw plate assembly as set forth in claim 10, wherein each of said pair of through holes includes upper and lower sections, the upper section including an interior surface threading extending, and wherein each of said coupling elements includes an exterior surface threading which is matable to said interior surface threading, whereby each of said coupling elements is insertable into said corresponding through hole via engagement of said interior and exterior surface threadings.

12. The polyaxial locking screw plate assembly as set forth in claim 10, wherein said lower section of each of said pair of through holes comprises a curved interior surface, having a semi-spherical contour, therein defining an annular lip at said bottom of the plate, said annular lip defining a support for polyaxially supporting said semi-spherical head portion of said screw.

13. The polyaxial locking screw plate assembly as set forth in claim 9, wherein each of said coupling elements comprises a bottom curved surface which, upon insertion of the coupling element into the corresponding hole of said plate, above the head portion of said screw, locks the screw within the hole while still permitting rotation of the head therein.

14. A polyaxial locking screw plate assembly for the immobilization of vertebral bones, via fixation to surfaces thereof, comprising:

a plate having an upper portion, a lower portion, a top surface and a bottom surface, said upper and lower portions each having at least one through hole;

a plurality of coupling elements, each of said coupling elements being insertable into a corresponding through hole; and a plurality of bone screws, each of said bone screws having a semi-spherical head portion and a shaft, said shaft portion being insertable through the corresponding through hole and into a vertebral bone, and said semi-spherical head portion being polyaxially supported within said corresponding through hole, such that the shaft of the bone screw may be selectively angulated within a predetermined range of angles relative to the plate, and wherein each of said coupling elements comprises a bottom curved surface, which bottom curved surface includes at least one attaching means protruding therefrom, whereby, upon insertion of the coupling element into the corresponding hole of said plate, locks the screw within the hole and locks the angle of the screw with respect to the plate.

15. The polyaxial locking screw plate assembly as set forth in claim 14, wherein said at least one attaching means comprises at least one spike extending outwardly from the bottom surface of said coupling element.

16. A polyaxial locking screw plate assembly for the immobilization of vertebral bones, via fixation to surfaces thereof, comprising:

a plate having an upper portion, a lower portion, a top surface and a bottom surface, said upper and lower portions each having at least one through hole;

a plurality of coupling elements, having a semi-spherical interior volume, each of said coupling elements being insertable into a corresponding through hole;

a plurality of bone screws, each of said bone screws having a semi-spherical head portion and a shaft, said shaft portion being insertable through the corresponding through hole and into the anterior portion of a vertebral bone, and said semi-spherical head portion being rotationally freely mounted within the semi-spherical interior volume of the coupling element so that the shaft of the bone screw and the coupling element may be inserted into a corresponding through hole and said shaft of the bone screw may be selectively angulated within a predetermined range of angles including non-perpendicular angles relative to the plate and thereby locking said coupling element and said semi-spherical head to said plate at said selected angle as said semi-spherical head and said coupling element are advanced into said corresponding through hole; and at least one attaching means protruding from the bottom surface of said plate for removable and temporary fixation of said plate to the vertebral bone.

17. The polyaxial locking screw plate assembly as set forth in claim 16, wherein said at least one attaching means comprises at least one spike extending outwardly from the bottom surface of said plate.

* * * * *